United States Patent
Harkema et al.

(10) Patent No.: US 11,007,368 B2
(45) Date of Patent: May 18, 2021

(54) METHODS FOR PROVIDING OPTIMIZED NEUROSTIMULATION

(71) Applicant: UNIVERSITY OF LOUISVILLE RESEARCH FOUNDATION, INC., Louisville, KY (US)

(72) Inventors: Susan J. Harkema, Louisville, KY (US); Yangshen Chen, Louisville, KY (US); Robert S. Keynton, Louisville, KY (US); Douglas J. Jackson, New Albany, IN (US); John Naber, Goshen, KY (US); Thomas Roussel, Louisville, KY (US); Manikandan Ravi, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 122 days.

(21) Appl. No.: 15/752,280

(22) PCT Filed: Aug. 18, 2016

(86) PCT No.: PCT/US2016/047535
§ 371 (c)(1),
(2) Date: Feb. 13, 2018

(87) PCT Pub. No.: WO2017/031306
PCT Pub. Date: Feb. 23, 2017

(65) Prior Publication Data
US 2018/0236241 A1    Aug. 23, 2018

Related U.S. Application Data

(60) Provisional application No. 62/206,937, filed on Aug. 19, 2015.

(51) Int. Cl.
*A61N 1/00*   (2006.01)
*A61N 1/36*   (2006.01)
*A61N 1/05*   (2006.01)

(52) U.S. Cl.
CPC ....... *A61N 1/36185* (2013.01); *A61N 1/0551* (2013.01); *A61N 1/3605* (2013.01);
(Continued)

(58) Field of Classification Search
CPC ........... A61N 1/36185; A61N 1/36146; A61N 1/3605; A61N 1/36175; A61N 1/36167; A61N 1/0551; A61N 1/3615
See application file for complete search history.

(56) References Cited

U.S. PATENT DOCUMENTS

2005/0070972 A1*  3/2005  Wahlstrand .......... G01R 33/285
                                                              607/48
2008/0049376 A1   2/2008  Stevenson et al.
(Continued)

FOREIGN PATENT DOCUMENTS

WO      2010/067360      6/2010

OTHER PUBLICATIONS

International Search Report and Written Opinion of the International Searching Authority for PCT/US2016/047535, dated Dec. 1, 2016.

*Primary Examiner* — Mallika D Fairchild
(74) *Attorney, Agent, or Firm* — Dentons Bingham Greenebaum LLP; Brian W. Chellgren

(57) ABSTRACT

Disclosed herein are methods for neurostimulation therapy for spinal cord injury. More particularly, the present invention relates to methods for neurostimulation therapy for spinal cord injury. More particularly, the present invention relates to methods for providing multiple independent, simultaneous waveforms in neurostimulation therapy while (Continued)

minimizing or substantially eliminating undesirable interactions between the waveforms.

19 Claims, 16 Drawing Sheets

(52) U.S. Cl.
CPC ..... *A61N 1/36146* (2013.01); *A61N 1/36167* (2013.01); *A61N 1/36171* (2013.01); *A61N 1/3615* (2013.01)

(56) References Cited

U.S. PATENT DOCUMENTS

| | | | | |
|---|---|---|---|---|
| 2011/0054567 | A1* | 3/2011 | Lane | A61B 5/0488 607/59 |
| 2011/0301662 | A1* | 12/2011 | Bar-Yoseph | A61N 1/0514 607/40 |
| 2015/0196767 | A1 | 7/2015 | Ahmed | |

* cited by examiner

C1

S1

C2

S2

METHODS FOR PROVIDING OPTIMIZED NEUROSTIMULATION

This application claims the benefit of U.S. provisional patent application Ser. No. 62/206,937, filed 19 Aug. 2015, for METHODS FOR PROVIDING OPTIMIZED NEUROSTIMULATION, incorporated herein by reference.

FIELD OF THE INVENTION

Embodiments of the present invention relate to methods for neurostimulation therapy for spinal cord injury. More particularly, embodiments of the present invention relate to methods for providing multiple independent, simultaneous waveforms in neurostimulation therapy while minimizing or substantially eliminating undesirable interactions between the waveforms.

BACKGROUND

Serious spinal cord injuries (SCI) result in partial (incomplete) or substantially complete loss of sensory motor function below the level of the spinal lesion. For individuals with incomplete loss of motor function, substantial recovery of standing and stepping recovery has been demonstrated with task specific physical rehabilitation training. Recently, task specific physical rehabilitation training has been combined with epidural stimulation (ES) of the spinal cord in patients with incomplete and complete motor paralysis. High density epidural stimulating electrode arrays can provide spatially selective stimulation to regions of the spinal cord to facilitate or cause muscle movement.

SCI and other conditions may benefit from the delivery of stimulus intended to enable or excite multiple neurological responses using an implantable neurostimulator. A targeted neurological function, such as blood pressure, may respond to a particular electrical stimulus or waveform at a specific location, amplitude, frequency, pulse width or a combination thereof. Other functions, such as muscle flexon, may require a different waveform to produce the desired response. For situations where multiple neurological functions need to be stimulated at the same time, the different stimulus signals may interfere and prevent the desired responses or even cause an undesired and potentially dangerous overstimulated condition.

The circuit shown in FIG. 1 is a simplified model of four electrodes being stimulated using two different waveforms for neurostimulation. A first waveform connects to electrode pair 4 and 3, while a second waveform connects to electrode pair 2 and 1. Node R is common to all electrodes, since all electrodes are in a common conductive medium, e.g., tissue and fluid. Interactions between each pair of electrode sets or waveforms can occur when electrodes are not isolated from connecting circuits. These coupled interactions between waveforms with overlapping pulses can add constructively or destructively to each other, depending upon if each pulse is in the charging or discharging phase. Moreover, this situation of overlapping pulses from multiple and simultaneous waveforms will result, at minimum, in undesired stimuli and could result in larger than intended and potentially dangerous stimuli from constructive interference in scenarios where the overlapping pulses add together. Overlapping pulses can also interfere destructively, which will limit the expected waveform amplitude delivered to the nerves. Overlapping pulses can also make charge balancing very complicated, as a clinician may not know the exact behavior of interactions between pulses. This scenario of overlapping pulses may occur routinely if each waveform is allowed to independently vary in frequency and pulse width.

The common approach in the industry for managing interaction between waveforms is to not allow overlap of stimulus pulses between electrode pairs or sets. One product, the Precision Spectra™ stimulator offered by Boston Scientific, allows for independent variation of the frequency and pulse width for up to four simultaneous waveforms. The product, as understood by the inventors, manages interactions between waveforms by detecting waveform overlap, defined as pulses within 3 milliseconds (ms) of each other, and if detected, automatically delaying one the pulses by 3 ms. This approach has several shortcomings, including (1) no user understanding of the effect this pulse delay has on the frequency change of the waveform—the more overlapping pulses are delayed, the greater the effect on the frequency change of the waveform—or even which waveform was affected, (2) no user control or feedback, as the waveform management is performed autonomously by hardware, (3) no pre-processing of the phase relationship between waveforms to minimize the number of overlap occurrences, (4) no option to select the length of the delay or select which of the overlapping pulses receives the delay, (5) no option to "blank" or refrain from emitting the overlapping pulse at a particular instant in time, (6) no ability to prioritize which of the overlapping waveforms will be blanked or phase shifted, (7) no ability to change the recharge width of the pulse, (8) no ability to change the shorting width of the pulse, and (9) no ability to accommodate global shorting windows. The assembly and delivery of sophisticated stimulation patterns while minimizing undesirable interactions between waveforms remains a challenge.

SUMMARY

Disclosed herein are methods for minimizing undesirable interactions between waveforms, particularly in neurostimulation therapy for spinal cord injury. Methods include modifying characteristics of independent, simultaneous waveforms with overlapping pulses, and hardware-based solutions for minimizing or substantially eliminating interactions between pulses.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

DETAILED DESCRIPTION OF THE PREFERRED EMBODIMENTS

Figure 1:
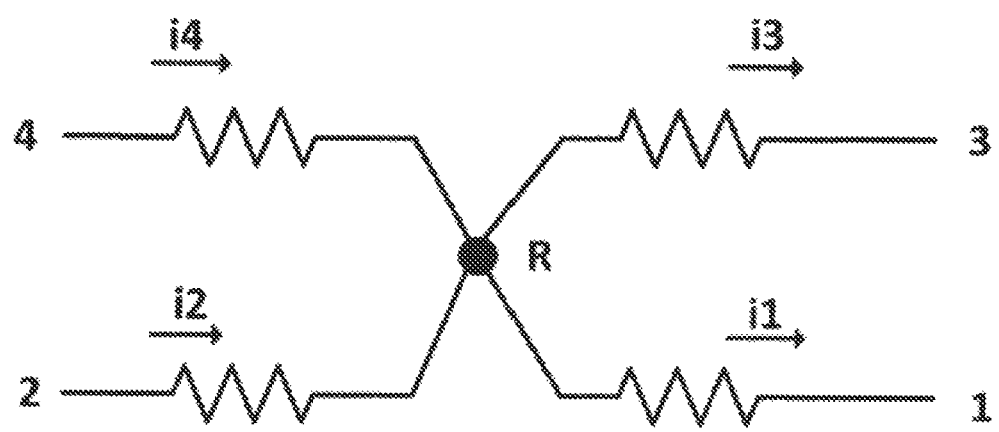
FIG. 1 is a schematic of an exemplary circuit for providing two simultaneous and independent waveforms.

For the purposes of promoting an understanding of the principles of the invention, reference will now be made to selected embodiments illustrated in the drawings and specific language will be used to describe the same. It will nevertheless be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document herein is a reference to an embodiment of a family of inventions, with no single embodiment including features that are necessarily included in all embodiments, unless otherwise stated. Further, although there may be references to "advantages" provided by some embodiments of the present invention, it is understood that other embodiments may not include those same advantages, or may include different advantages. Any advantages described herein are not to be construed as limiting to any of the claims.

Specific quantities (spatial dimensions, angles, dimensionless parameters, etc.) may be used explicitly or implicitly herein, such specific quantities are presented as examples and are approximate values unless otherwise indicated. Discussions pertaining to specific compositions of matter are presented as examples and do not limit the applicability of other compositions of matter, especially other compositions of matter with similar properties, unless otherwise indicated.

The present invention comprises methods for minimizing undesirable interactions between waveforms, particularly in nerve stimulation therapy for spinal cord injury. In nerve stimulation therapy, an electrode array comprising a plurality of electrodes disposed on a flexible biocompatible material is provided. Preferably, the electrodes comprise one or more biocompatible metals or alloys, as known in the art. Sets of electrodes within the array generate waveforms, the electrode array being configured to generate at least two simultaneous waveforms, each waveform having a frequency, a pulse width, a phase and at least one pulse.

The electrode array and resulting waveforms may be optimized to reduce overlapping pulses between waveforms by software or hardware-based solutions. In some embodiments, waveforms are optimized by at least one of altering the phase of the waveform, altering the frequency of the waveform, altering the pulse width of the waveform, delaying a pulse of the waveform and blanking a pulse of the waveform.

Figure 2:
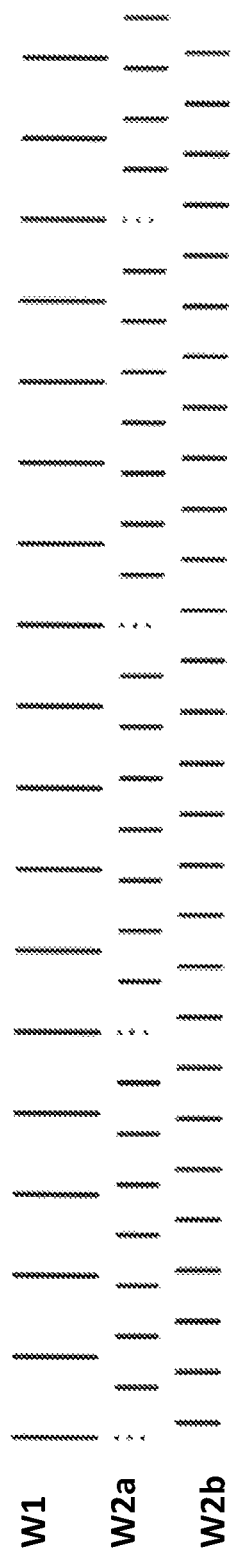
FIG. 2 is a schematic displaying pulses of waveforms W1 and W2a and phase optimized waveform W2b. Individual pulses are depicted as lines, with dotted lines depicting pulse collisions between W1 and W2a which are avoided in phase optimized waveform W2b.

The first method of waveform optimization is phase optimization. This method uses a computed delay to find the optimal position of waveforms relative to each other for the purpose of avoiding as many overlapping pulses as possible. Waveforms are assigned a priority and their phase is adjusted to optimize the higher priority waveform first. Referring to FIG. 2, the top waveform (W1) is designated the high priority waveform and remains unchanged. A lower priority waveform, W2, has a designated phase and collisions (overlapping pulses) between waveforms are predicted and counted. W2a shows three collisions with W1, as indicated by the vertical dashed lines, where pulses from W2a overlap with pulses from W1. The waveform then has its phase delayed by an increment and the collisions are recounted in W2b. The phase delay results in no collisions between W2b and W1 in the time period shown. In some embodiments, the delay that results in the fewest number of collisions is considered the optimized phase delay and can be set to automatically be adopted by the system or controlled manually. When a collision does occur, the lower priority offending pulse can either be "blanked" or eliminated, or phase shifted forward or backward in time to avoid overlapping, depending on which option is therapeutically preferable for the patient. Additional waveforms of lower priority can be tested against W1 and the optimized W2b to obtain the optimal delay for the additional waveforms.

The steps in this method can be summarized as follows: (1) count the number of collisions between two waveforms, W1 and W2, over a period of time T; (2) delay the lower priority waveform, in this case W2, an increment and recount collisions in period T; (3) repeat steps 1 and 2 until the increment reaches the period of the highest frequency waveform being compared; (4) adopt the delay (also referred to as "phase shift") that results in the lowest number of collisions; and (5) blank specific pulses from the W2 (the lower priority waveform) to remove the collision in order to produce a corrected W2. In the event that an additional waveform is used, steps 1-5 are repeated such that the additional waveform is compared to W1 and corrected W2, a phase shift is adopted for the additional waveform that minimizes collisions with higher priority waveforms, and overlapping pulses are blanked to produce a corrected additional waveform. The steps may be repeated as needed for further simultaneous waveforms.

A second method of waveform optimization is an alternating frequency approach. In this method, the frequency of a lower priority waveform is varied to avoid overlapping with the higher priority waveform. In some embodiments, the lower priority waveform varies between two predetermined frequencies to avoid collisions with a higher priority waveform. Combining two frequencies on one waveform allows an interval to form so that no blanking or delayed reset is required. This two frequency approach eliminates a missing pulse and hence small gaps with no active stimulus.

Figure 3:
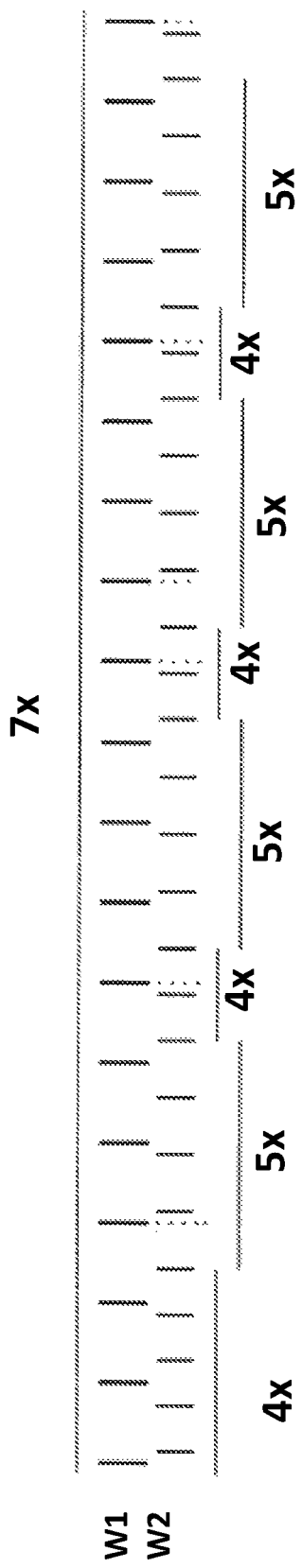
FIG. 3 is a schematic displaying pulses of waveform W1 and frequency optimized waveform W2. Individual pulses are depicted as lines, with dotted lines depicting pulse collisions avoided by frequency optimization of W2.

Referring now to FIG. 3, two waveforms W1 and W2 are frequency optimized. In this example, W1 is the higher priority waveform and its frequency does not change. In the depicted example, the period of W1 is 7x. W2 is a lower priority waveform that is allowed to change between two fixed frequencies with periods 4X and 5X. When a collision is computed to occur, represented in FIG. 3 by a dashed line, the other frequency is selected. That is, if a pulse overlap is expected to occur while maintaining the 4X period, the W2 waveform is transitioned to the 5X period prior to the overlap to avoid the collision. Subsequently, if a collision is estimated to overlap at the 5X period, the waveform is transitioned back to the 4X period. This produces a waveform with two alternating frequencies. The choice of frequencies may be based on the effectiveness of the chosen frequencies on neurostimulation, in that a small frequency change may not be detrimental to therapy, and based on selecting frequencies which correct the timing and minimize the number of collisions. While this method is primarily designed to avoid pulse collisions, varying the frequency of a waveform may also be used to intentionally create a desired neurostimulatory response.

The third method for managing waveforms is a charge balance time optimization approach. A typical neurostimulation pulse includes a wait period (X), charge pulse (1), inter-pulse delay (0.05), a recharge pulse (4), and a shorting period (4). The numbers correspond to the relative length of that portion of the pulse, with the length of the wait period being variable. The duration of the pulse and subsequent delay, recharge pulse and shorting period are determined by neurological needs and the need to balance charge on the electrode. In some cases it is possible to shorten pulses or parts of pulses to help eliminate overlap conditions between waveforms. In particular, the charge balance portion of the pulse (i.e., the recharge pulse and shorting period) may be reduced. For example, the recharge pulse (also referred to as the recharge period) could be reduced from (4) to (3) and the shorting period from (4) to (2) resulting in an approximate 33% reduction in duration for the active portion of the pulse. Brief periods of charge balance time optimization may be used to allow spacing between pulses from different waveforms and reduce the need to blank a pulse.

Figure 4:
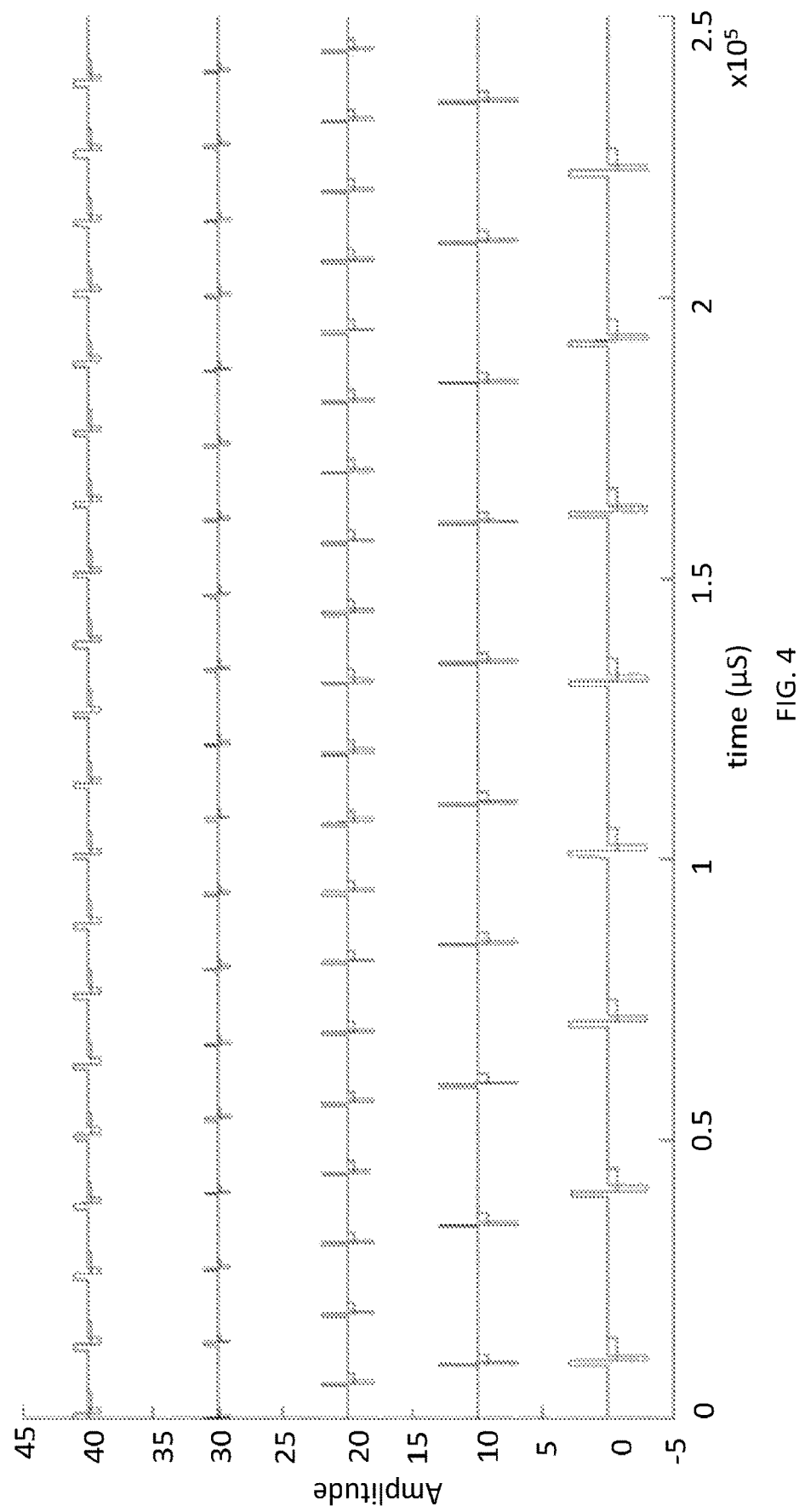
FIG. 4 is a chart depicting five simultaneous waveforms, with optimized and non-optimized versions of the waveforms superimposed.

The percentage of overlap of two colliding pulses is an indicator as to the effectiveness of using charge balance time optimization as a solution. Referring now to FIG. 4, the pulse collision between five simultaneous waveforms can be reduced by over 90% by just changing the adjustable recharge period from (4) to (1). The recharge period is visible as the relatively small period of decreased amplitude directly following each pulse. Decreasing the recharge period increases the available time window from only 3.5% to 65% to incorporate global shorting and to minimize any residual electrode charge. Commercial neurostimulators typically use a recharge pulse length of (4) to amply ensure that charge has been removed from the electrode and to minimize power consumption. However, the ability to vary the width of the recharge pulse and shorting pulse provides clinicians with tremendous flexibility in managing waveforms to reduce overlaps. For example, a system may operate in a high power mode with a short recharge pulse length of (1) when managing multiple complex waveforms with long charge pulses and many pulse overlaps, and switch to a low power mode using a long recharge pulse length of (4) when managing few waveforms with short charge pulses and few pulse overlaps.

A fourth method of managing waveform interactions is by blanking a lower priority waveform. In this method, upon detection, calculation or prediction of an overlap of pulses between a higher priority waveform and a lower priority waveform, the pulse of the lower priority waveform is blanked. However, blanking a pulse can result in a small signal void that may be undesirable. Another option to blanking an overlapping pulse is to add a pulse to delay the waveform so it can be reset to restart the waveform in its initial position. This is similar to the two frequency approach described in the second method. However, in this case, the frequency that is produced by the corrected delay occurs for one period and is calculated on a collision by collision basis.

FIGS. 5-8 display the results of these various methods in optimizing three simultaneous waveforms, one with a frequency of 25 Hz, a second with a frequency of 33 Hz, and a third with a frequency of 55 Hz, with respective pulse widths of 1000 microseconds, 750 microseconds, and 200 microseconds. In this example, the 55 Hz waveform is considered the highest priority waveform. FIG. 5A depicts pulses from the three waveforms, each with recharge period of 4 and a shorting period of 4. FIG. 5B depicts collisions between pulses from the three waveforms. In this unoptimized arrangement, the rate of pulse collisions between the 25 Hz and 33 Hz waveforms is 52%, the rate of pulse collisions between the 25 Hz and 55 Hz waveforms is 60% and rate of pulse collisions between the 33 Hz and 55 Hz waveforms is 67%.

Figure 5A:
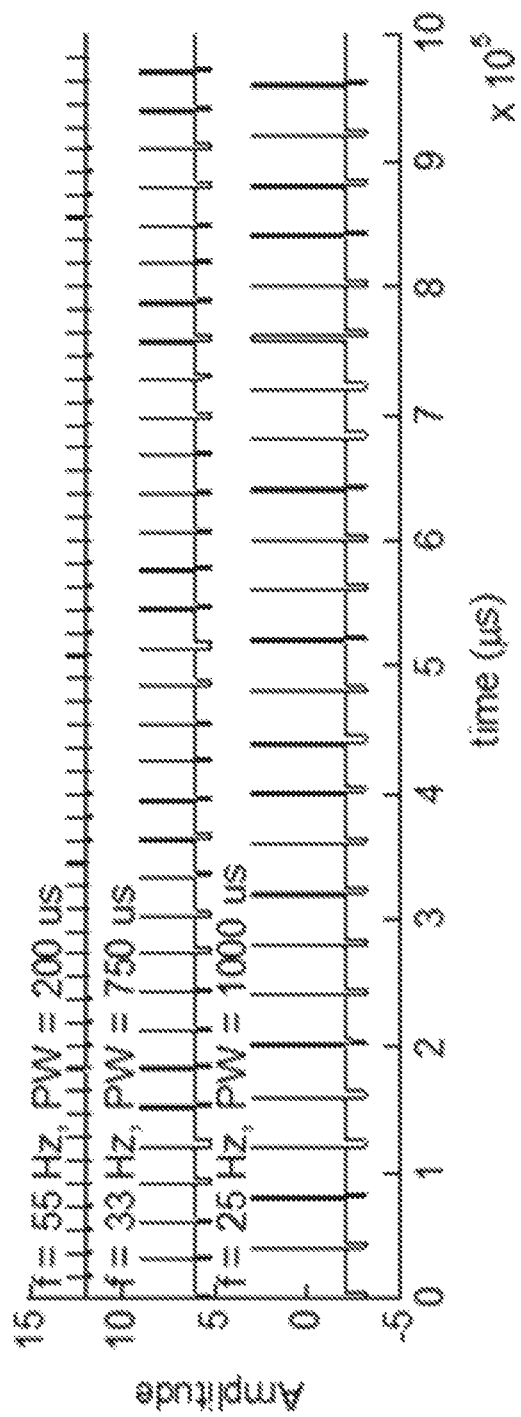
FIG. 5A is a chart depicting three simultaneous waveforms generated by a neurostimulator with (top) a frequency of 55 Hz and a pulse width of 200 µs, (middle) a frequency of 33 Hz and a pulse width of 750 µs, and (bottom) a frequency of 25 Hz and a pulse width of 1000 µs.
Figure 5B:
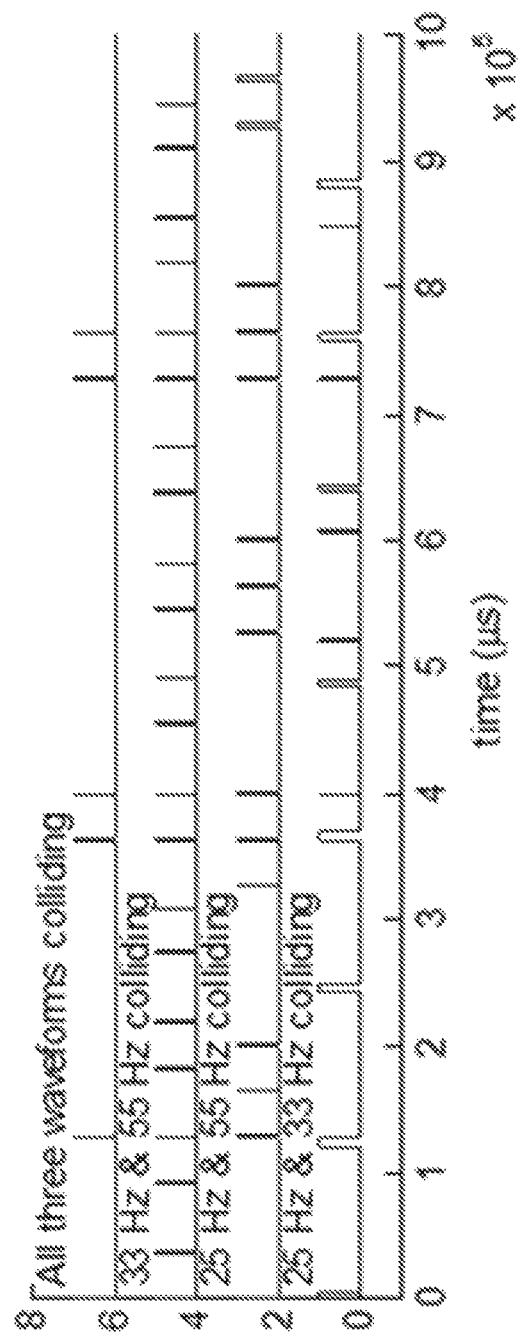
FIG. 5B is a chart depicting pulse collisions between the waveforms of FIG. 5A, with the top line displaying collisions between all three waveforms, the next lower line displaying collisions between the 33 Hz and 55 Hz waveforms, the next lower line displaying collisions between the 25 Hz and 55 Hz waveforms, and the bottom line displaying collisions between the 25 Hz and 33 Hz waveforms.
Figure 6A:
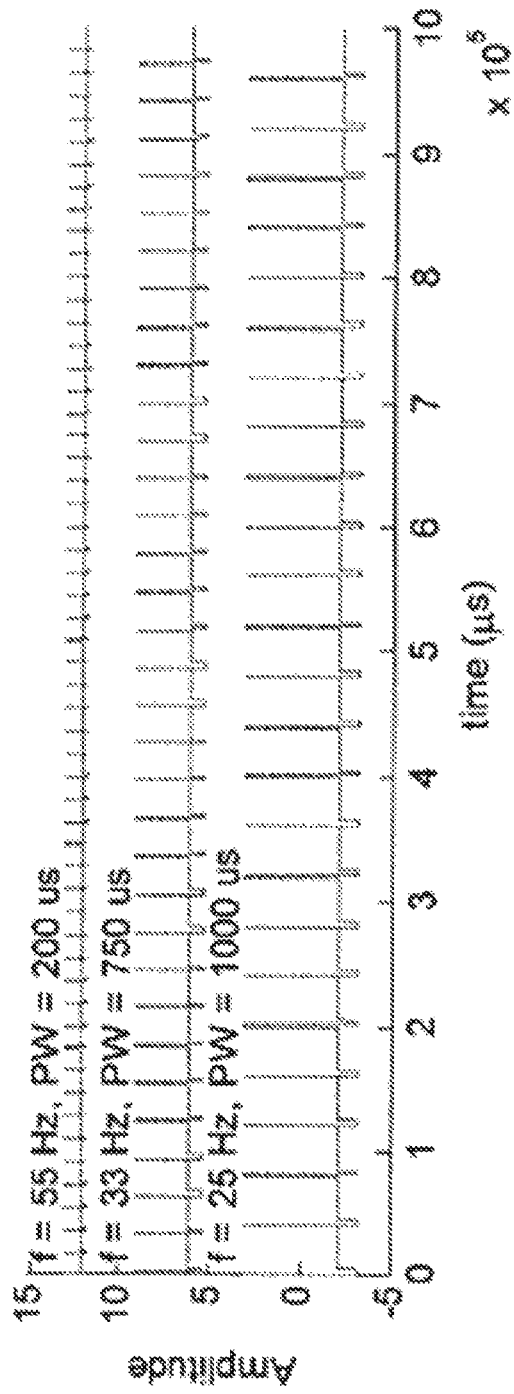
FIG. 6A is a chart depicting the three waveforms of FIG. 5A after phase optimization of the 33 Hz waveform.
Figure 6B:
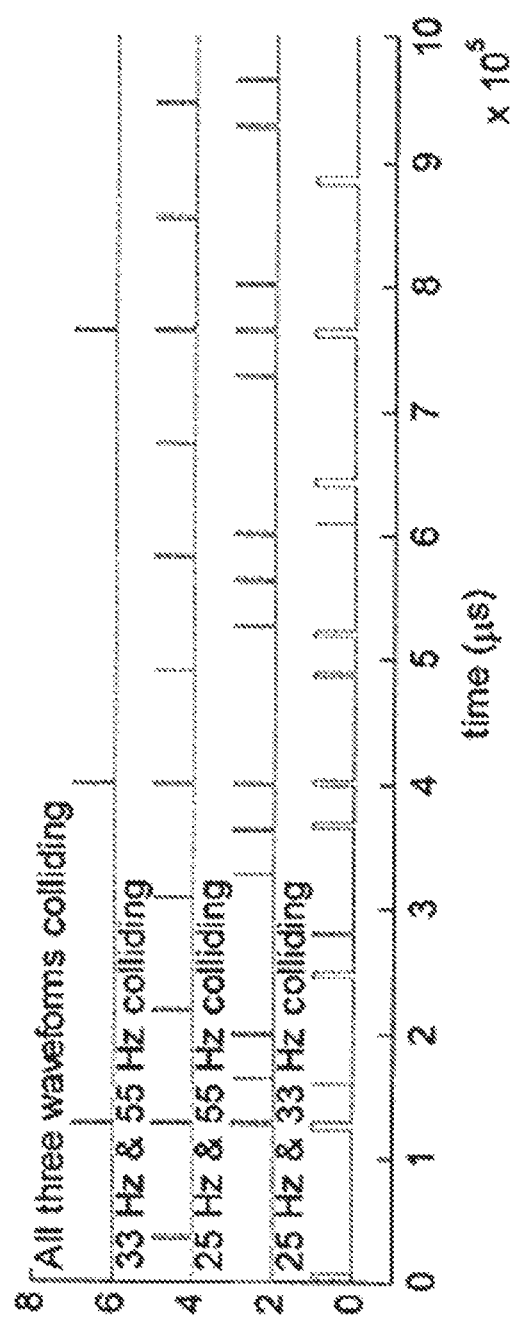
FIG. 6B is a chart depicting pulse collisions between the waveforms of FIG. 6A, with the top line displaying collisions between all three waveforms, the next lower line displaying collisions between the 33 Hz and 55 Hz waveforms, the next lower line displaying collisions between the 25 Hz and 55 Hz waveforms, and the bottom line displaying collisions between the 25 Hz and 33 Hz waveforms.

FIG. 6A depicts the three waveforms from FIG. 5A after undergoing phase optimization. The 33 Hz waveform has been delayed to decrease collisions with the highest priority waveform, that being the 55 Hz waveform. The frequencies, pulse widths, recharge periods and shorting periods remain unchanged. As shown in FIG. 6B, the number of collisions between pulses in the 55 Hz and 33 Hz waveforms has decreased significantly. In this phase optimized arrangement, the rate of pulse collisions between the 25 Hz and 33 Hz waveforms remains unchanged at 52%, the rate of pulse collisions between the 25 Hz and 55 Hz waveforms remains unchanged at 60% and rate of pulse collisions between the 33 Hz and 55 Hz waveforms has decreased to 33%, a 34% reduction as compared to the unoptimized arrangement in FIGS. 5A-B. Further reduction of collisions may be achievable by phase optimization of the 25 Hz waveform against the 55 Hz waveform and the optimized 33 Hz waveform.

Figure 7A:
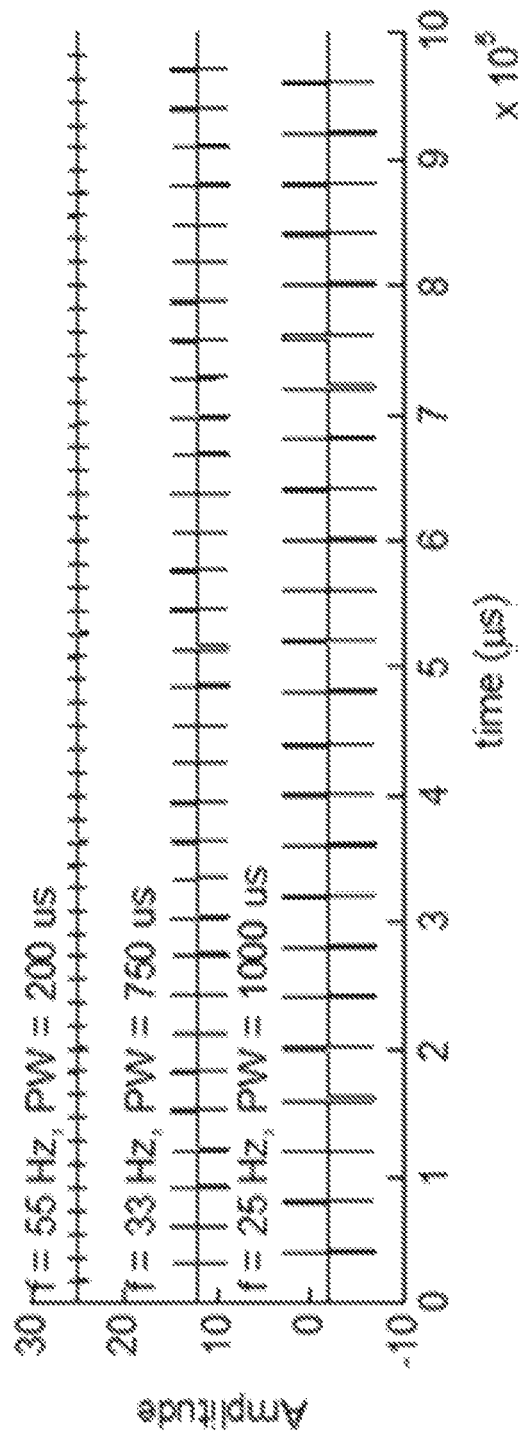
FIG. 7A is a chart depicting the three waveforms of FIG. 5A after pulse width optimization of the three waveforms.
Figure 7B:
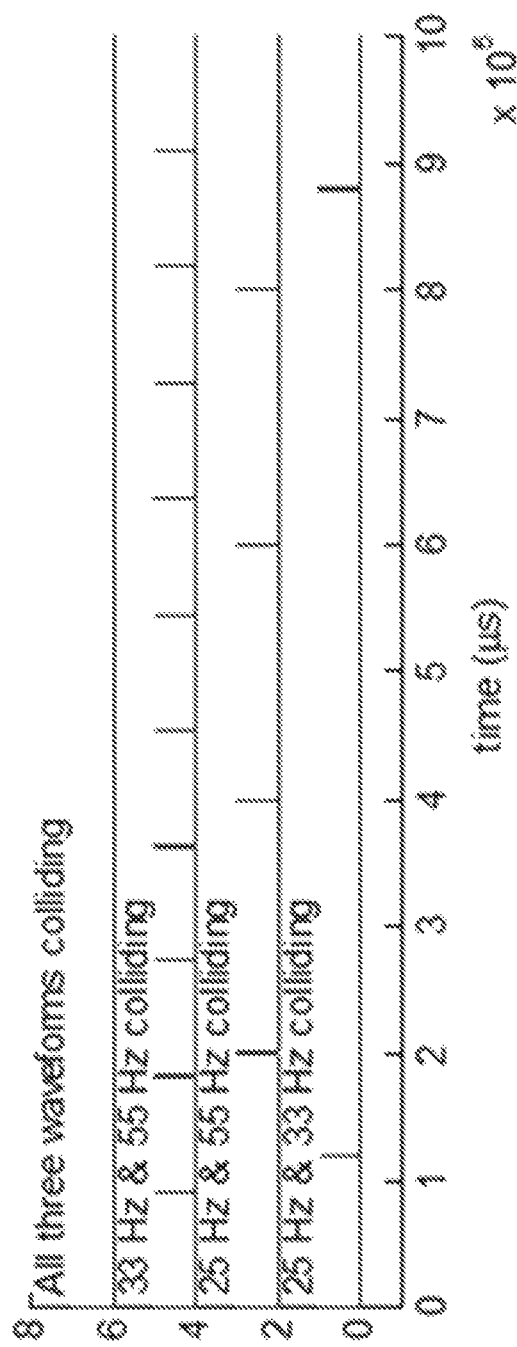
FIG. 7B is a chart depicting pulse collisions between the waveforms of FIG. 7A, with the top line displaying collisions between all three waveforms, the next lower line displaying collisions between the 33 Hz and 55 Hz waveforms, the next lower line displaying collisions between the 25 Hz and 55 Hz waveforms, and the bottom line displaying collisions between the 25 Hz and 33 Hz waveforms.

FIG. 7A depicts the three waveforms from FIG. 5A after undergoing charge balance time optimization. The recharge period has been decreased to (1) and the shorting period has been decreased to (0). The frequencies and onset times of the waveforms remain unchanged, as do the pulse widths of the recharging pulses. As shown in FIG. 7B, the number of collisions between pulses has decreased significantly for all three waveforms. In this pulse width optimized arrangement, the rate of pulse collisions between the 25 Hz and 33 Hz waveforms has decreased to 12%, the rate of pulse collisions between the 25 Hz and 55 Hz waveforms remains has decreased to 20% and rate of pulse collisions between the 33 Hz and 55 Hz waveforms has decreased to 33%. Further reduction of collisions may be achievable by phase optimization of the 25 Hz waveform against the 55 Hz waveform and the optimized 33 Hz waveform.

Figure 8A:
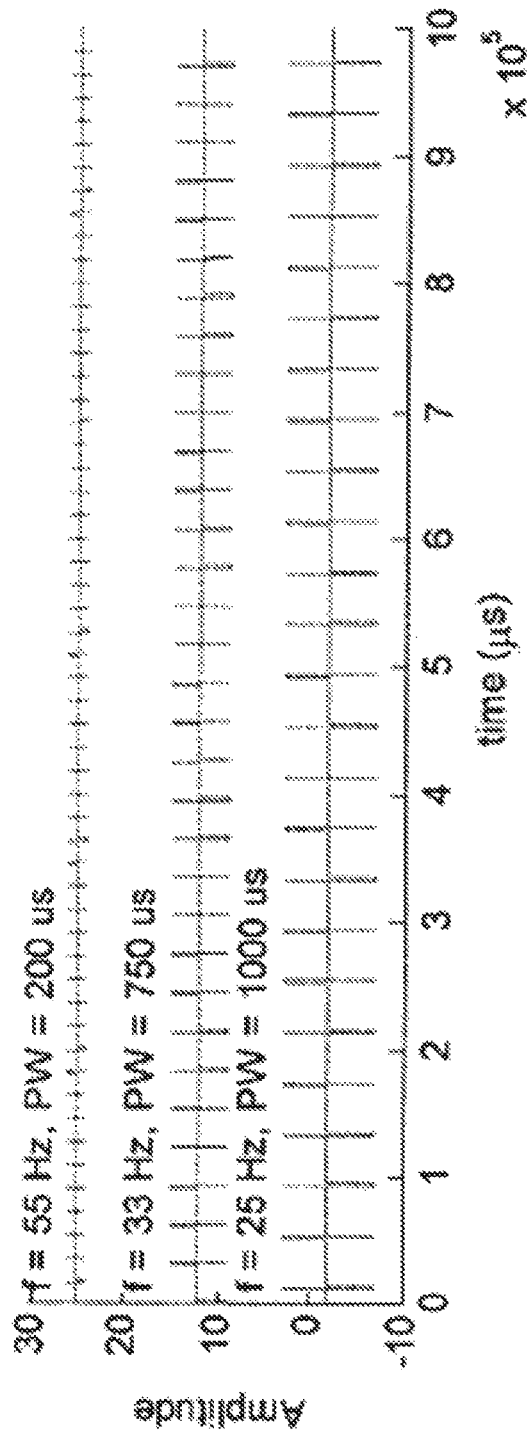
FIG. 8A is a chart depicting the three waveforms of FIG. 5A after pulse width optimization and phase optimization of the three waveforms.
Figure 8B:
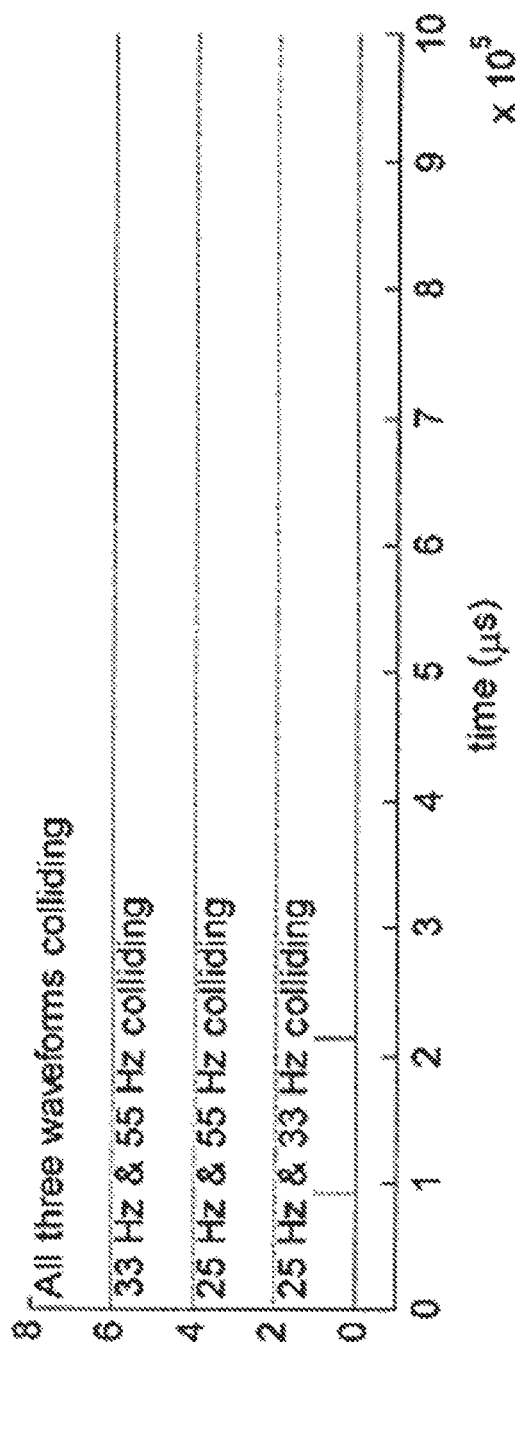
FIG. 8B is a chart depicting pulse collisions between the waveforms of FIG. 8A, with the top line displaying collisions between all three waveforms, the next lower line displaying collisions between the 33 Hz and 55 Hz waveforms, the next lower line displaying collisions between the 25 Hz and 55 Hz waveforms, and the bottom line displaying collisions between the 25 Hz and 33 Hz waveforms.

FIG. 8A depicts the three waveforms from FIG. 5A after undergoing charge balance time optimization and phase optimization. The recharge period has been decreased to (1) and the shorting period has been decreased to (0) for all three waveforms. In addition, the 33 Hz waveform has been delayed to decrease collisions with the 55 Hz waveform, and subsequently the 25 Hz has been delayed to decrease collisions with the 55 Hz and 33 Hz waveforms. The frequencies of the waveforms remain unchanged. As shown in FIG. 8B, the number of collisions between pulses has decreased significantly for all three waveforms. In this pulse width optimized and phase optimized arrangement, the rate of pulse collisions between the 25 Hz and 33 Hz waveforms has decreased to 8%, and all pulse collisions between the 55 Hz waveform and the other two waveforms have been eliminated. In some embodiments, the remaining overlapping pulses between the 25 Hz and 33 Hz waveforms may be blanked or delayed in the lower priority waveform to eliminate all overlaps.

In some embodiments the priority of waveforms may be changeable. In the examples depicted in FIGS. 2 and 3, W1 is defined as the high priority waveform and thus no alterations such as blanking, phase shift, delay or frequency shift are applied to that waveform. In practice, it may be advantageous to change the priority of a waveform based on factors such as the rate that modifications are occurring to a given waveform, time since last modification of a given waveform, or implantable pulse generator (IPG) commands for particular tasks. For example, a newly activated waveform may begin with a high priority, then may reduce in priority over time. For another example, when a first waveform experiences a high number of alterations, the system could trigger a second, higher priority waveform to reduce its priority in order to decrease the number of alterations to the first waveform.

Pulse collisions are typically avoided to isolate patient stimuli and maintain a balanced charge on neurostimulator electrodes. However, a purposeful pulse collision may be used to determine details about the equivalent circuit of the array or study the impact of field shapes on neuro responses. For this reason it may be desirable to generate collisions under controlled conditions.

The first four methods of optimization disclosed herein may be implemented in software controlling an implanted neurostimulator. In some embodiments, a technical user interface (TUI), such as a general purpose computer, or a patient user interface (PUI), such as a portable dedicated computing device, a smartphone or other portable computing device, run software communicatively coupled to the implanted neurostimulator and capable of adjusting the characteristics of waveforms generated by the neurostimulator. In some embodiments, the clinicians initially use the TUI in a clinical setting to evaluate the SCI patients to identify the set of waveforms necessary to generate responses from the patient, such as standing, leg flexion, leg extension, blood pressure control, bladder control, etc. Overlapping pulses often occur when generating multiple simultaneous pulses that have different frequencies that are not harmonically related to each other, as shown in FIGS. 5A and 5B.

The optimum set of waveforms and their characteristics (e.g., frequency, amplitude, phase, delay, and pulse width) are unique to each patient. The clinician uses the TUI to identify waveforms needed by a patient to elicit a desired response, such as waveforms stimulating leg muscles to elicit a walking motion, in conjunction with waveforms maintaining the patient's blood pressure at a safe level. The clinician determines the priority of the various wave forms based on the patient's physiological needs. For example, waveforms maintaining blood pressure are more critical to the patient's health than waveforms eliciting a walking motion so blood pressure-related waveforms will be designated as higher priority than walking-related waveforms. These waveforms are then optimized using one or more of the methods described above. Once these optimized waveforms are determined, they can be transferred from the TUI to the PUI for the patient to activate at the patient's discretion. In preferred embodiments, the patient uses the PUI to select what motor responses, such as standing or walking, or physiological responses, such as blood pressure control, that he or she wishes to enact, and the PUI instructs the patient's implanted neurostimulator to enact the predetermined waveforms to enact such responses in the patient. In a preferred embodiment, PUI is configured such that the patient can only run waveforms optimized by the TUI, and the patient cannot create or modify waveforms or combinations thereof.

Using the TUI to manage the overlapping pulse waveforms provides clinicians with control over how the overlapping waveforms are modified to reduce or eliminate the problem. In some embodiments, the TUI runs software is designed to display waveforms and show what percentage of overlap exists and where the overlap occurs in time, as shown in FIGS. 5-8. The clinician is then presented options as described in methods one through four to reduce or eliminate the number of overlapping pulses. Once the waveforms are optimized, they are transmitted from the TUI to a base station, which wirelessly transmits the data to the IPG. In other embodiments, the first four methods of optimization disclosed herein may be implemented in the hardware of the neurostimulator such as, by algorithmic detection of pulse collisions and implementation of methods to minimize collisions. In such embodiments, unoptimized waveforms are transmitted to the neurostimulator and a controller, such as a microprocessor, included in the neurostimulator optimizes the waveforms before delivery of electric stimulation to the patient.

Figure 9A:
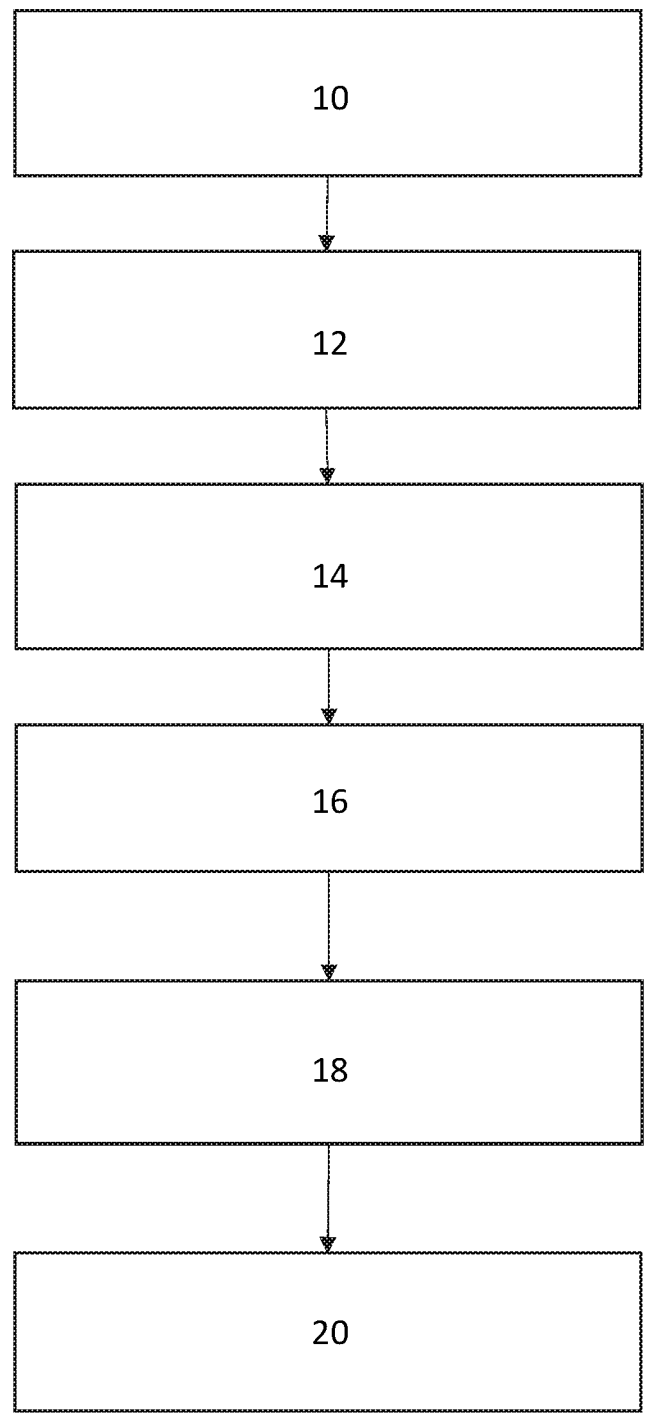
FIG. 9A is a flowchart depicting an exemplary method for optimizing waveforms.
Figure 9B:
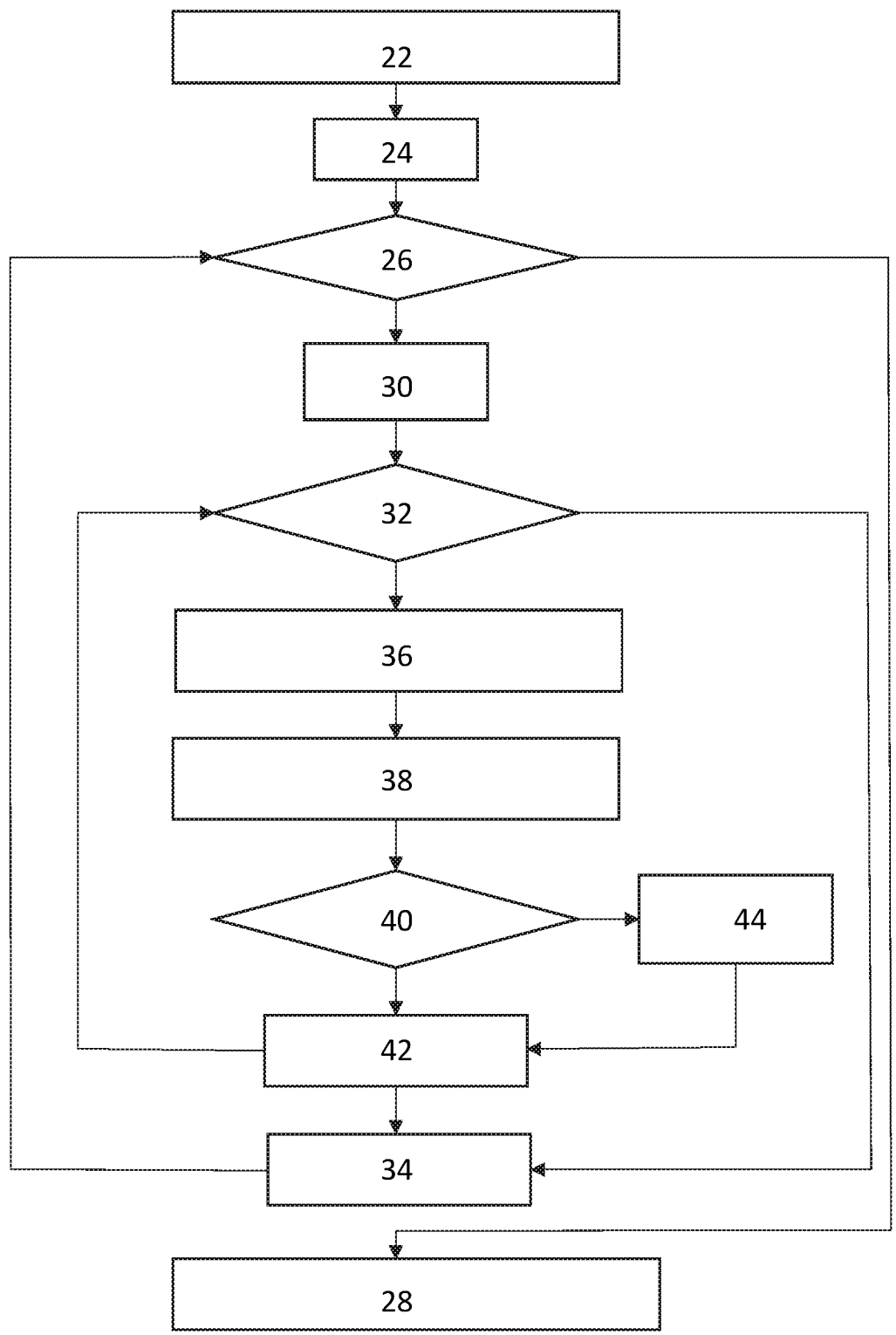
FIG. 9B is a flowchart depicting an exemplary phase optimization process.

FIGS. 9A and 9B provide an embodiment of a method for optimizing waveforms, with FIG. 9B providing an exemplary initial phase delay optimization program, as referenced in step 3 in the flowchart of FIG. 9A. The exemplary program depicted in FIG. 9B is specific to only the initial phase delay optimization for minimization of pulse overlaps, and, in other embodiments, significantly more complex programs would be used.

Referring now to FIG. 9A, in initial step 10, a user identifies two or more waveforms for delivery to a patient, and designates electrodes to provide the waveforms, setting pulse width, frequency, amplitude, waveform priority, onset and offset times, and other relevant settings. In step 12, the user sets a recharge period for active charge balance for the activating electrodes and sets a local shorting period for passive charge balance for the activating electrodes. The recharge period is typically (1), (2) or (4), with (4) being the most common initial value of an unoptimized waveform. The shorting period is typically (0), (1), (2) or (4), with (4) being the most common initial value of an unoptimized waveform. In step 14, the user performs a phase optimization to add a delay to waveforms, apart from the highest priority waveform, as explained in further detail in connection with FIG. 9B. In step 16, the user reviews the simulated collisions after phase optimization. If the percentage of pulses colliding is greater than a predetermined value, such as greater than 20%, greater than 25%, greater than 30%, or greater than 50%, then optimization is not performed and the process is begun again using non-identical waveforms. In step 18, pulses on lower priority waveforms which collide with pulses on higher priority waveforms are blanked. In step 20, the optimized waveforms are transmitted to the neurostimulator. In certain embodiments, the optimized waveforms are transmitted from the TUI to a base station by a wired or wireless connection, then transmitted by a wireless connection between the base station and the neurostimulator. In certain embodiments, the user is a clinician or other medical professional trained in neurostimulation techniques. In some embodiments, the waveforms are optimized by phase optimization, pulse width optimization, frequency optimization, blanking colliding pulses, or a combination thereof. In certain embodiments, the waveforms are optimized by performing at least two different optimization processes.

FIG. 9B depicts an exemplary phase optimization process for two waveforms as performed in step 14 of the flowchart shown in FIG. 9A. The two waveforms differ in frequency, and are designated as the high frequency waveform and the low frequency waveform. In step 22, the wavelength of the high frequency waveform is calculated using techniques known in the art (in signal processing, wavelengths are typically measured in units of time, not distance). In subsequent step 24, a first counting variable is assigned a value of zero. Subsequent step 26 is a Boolean determination of whether the first counting variable is less than the calculated wavelength: if false, the process proceeds to step 28 and outputs the optimum shifting position, and if true, the process proceeds to step 30. In step 30, a second counting variable is assigned a value of zero. Subsequent step 32 is a Boolean determination of whether the second counting variable is less than the calculated wavelength: if false, the process proceeds to step 34, and if true, the process proceeds to step 36. In step 34, first counting variable is increased by a first increment, then the process returns to step 26. In step 36, the onset time of the low frequency waveform is delayed by the sum of the first counting variable and the second counting variable. In subsequent step 38, the number of pulse collisions between the high frequency waveform and delayed low frequency waveform is calculated. Subsequent step 40 is a Boolean determination of whether the number of collisions calculated immediately prior in step 38 is less than the number of previously calculated collisions: if false, the process proceeds to step 42, and if true, the process proceeds to step 44. In step 42, the second counting variable is increased by a second increment, then the process returns to step 32. In step 44, the optimum shifting position (initially set as zero) is defined as the sum of the first counting variable and the second counting variable, then the process proceeds to step 42 and continues cycling. When the process eventually reaches step 28, increments of shifting ranging from no shifting to shifting the entire wavelength of the high frequency waveform have been evaluated, and the outputted optimum shifting position is the shifting position which resulted in the lowest number of collisions.

In some embodiments, the process depicted in FIG. 9B may be repeated to optimize multiple waveforms. For example, the process may be run a first time to optimize a second-highest frequency waveform against a highest frequency waveform. The process may subsequently be run a second time to optimize a third-highest frequency waveform against the highest and second-highest frequency waveforms. The process may be run additional time to optimize still lower frequency waveforms against higher frequency waveforms until some or all of the simultaneous waveforms in a given neurostimulation have been optimized. Stepwise evaluation processes similar to that shown in FIG. 9B may be used for pulse width optimization, frequency optimization and blanking pulses to reduce pulse collisions.

Figure 10:
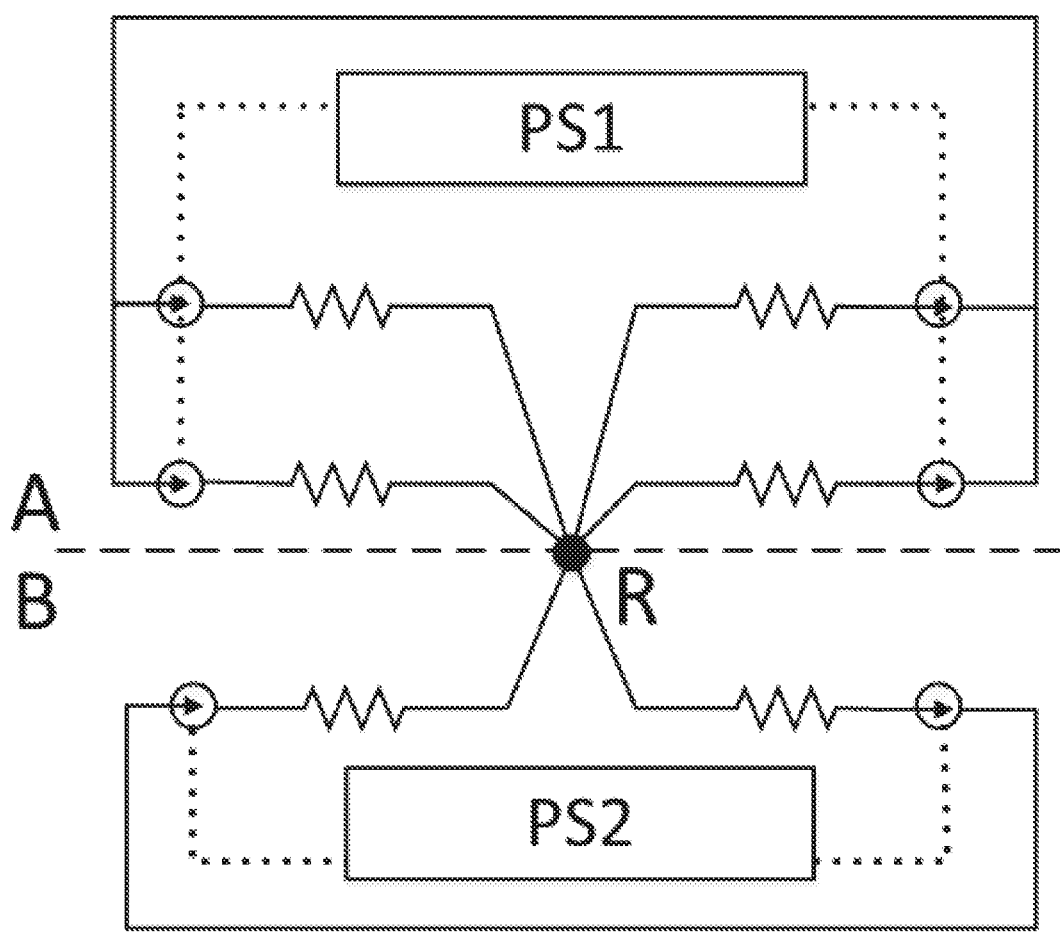
FIG. 10 is a schematic of an exemplary circuit including two separate and isolated power sources.

Embodiments of the present invention relate to hardware-dependent methods of managing waveform interactions. In a fifth method for optimization, independent and isolated power supplies are used to correct the overlapping pulse issue. Referring now to FIG. 10, an exemplary electrode diagram is shown including two separate and isolated power sources, PS1 and PS2, which are connected to the current sources by dotted lines. Although the electrodes 1, 2, 3, 4, 5 and 6, share a single common node R, there is only one connection, so there is no return path for current and this stimuli between sections A and B remain isolated. This method requires a separate and isolated power source for each electrode group containing common frequencies and pulse widths. In this example, group A has four electrodes 1, 2, 3 and 4 with a common first frequency and first pulse width, and group B has two electrodes 5 and 6 with a common second frequency and second pulse width. In some embodiments, the first and second frequencies are non-identical. In certain embodiments, the first and second pulse widths are non-identical. This method depends upon the accuracy of the common node model for the electrode array. If electrodes of section A are in close physical proximity to electrodes of section B, the accuracy of the model may degrade and some interaction between the waveforms, also referred to as "cross talk," may occur. In some embodiments, undesirable cross talk occurs when adjacent electrodes are powered by separate and isolated power sources. In other embodiments, undesirable cross talk occurs when electrodes powered by a separate and isolated power source are located within 0.5 cm, within 1.0 cm, or within 1.5 cm of electrodes powered by another separate and isolated power source.

Figure 11A:
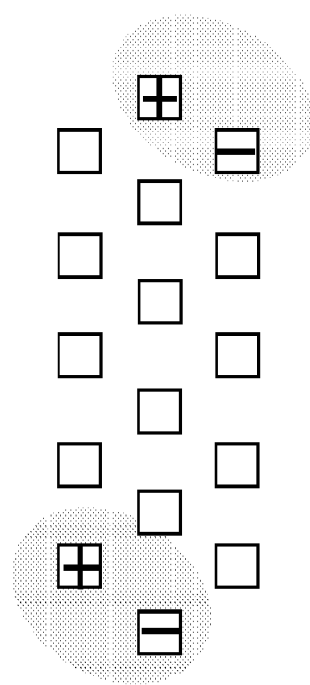
FIG. 11A depicts a schematic of an electrode array with two independent power supplies.
Figure 11B:
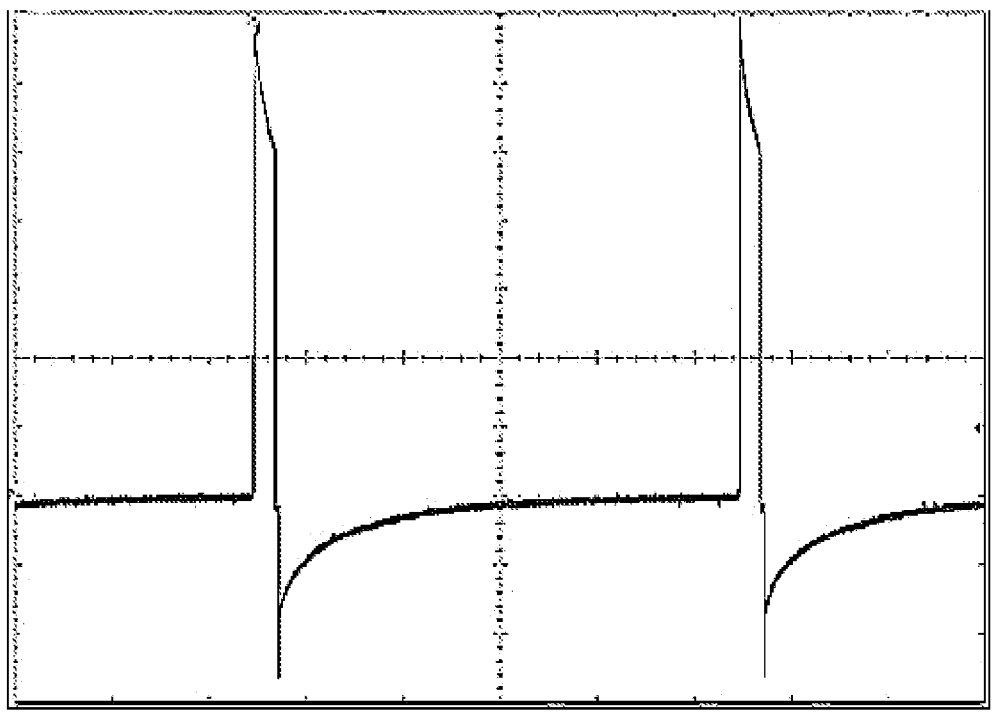
FIG. 11B depicts an oscilloscope trace from activation of the first electrode array shown in FIG. 11A.
Figure 11C:
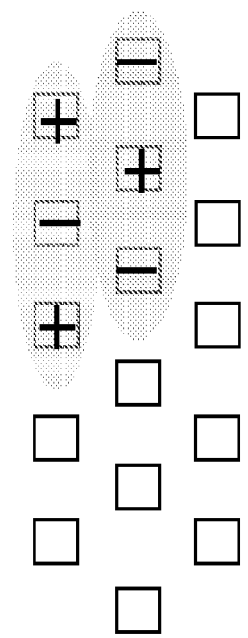
FIG. 11C depicts a schematic of a second electrode array with two independent power supplies.
Figure 11D:
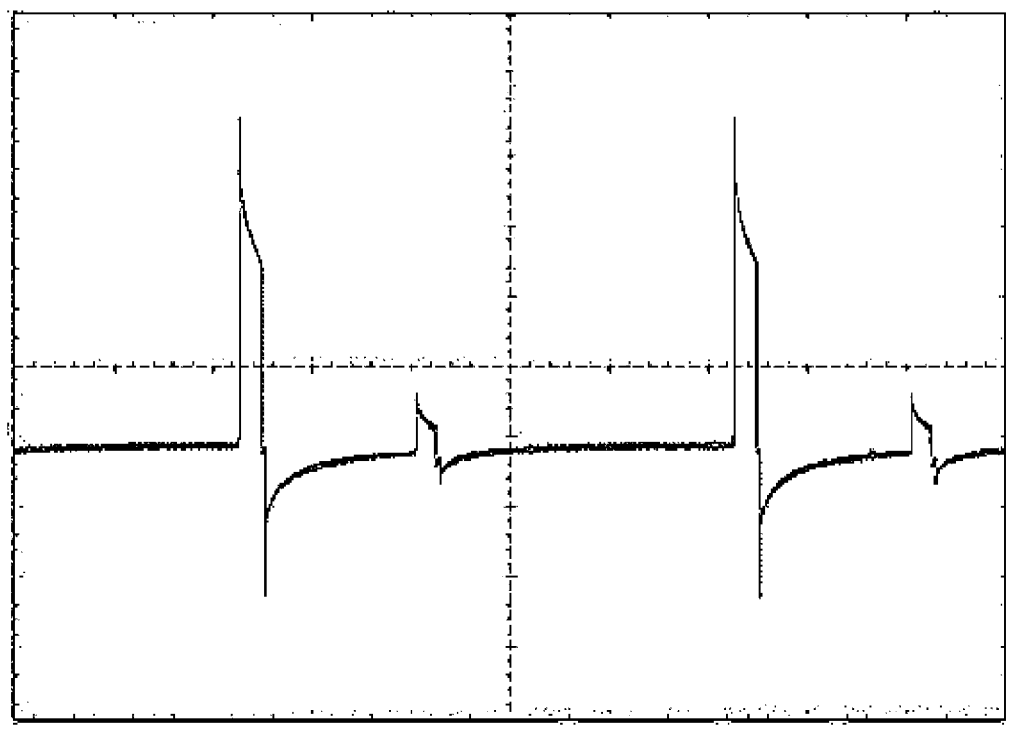
FIG. 11D depicts an oscilloscope trace from activation of the second electrode array shown in FIG. 11C.

Examples of this fifth method for optimization are shown in FIGS. 11A-11D and FIGS. 12A-12C. FIG. 11A depicts an array of electrodes wherein a pair of electrodes at the top of the array, as indicated by a grey oval, are stimulated by a first IPG and another pair of electrodes at the bottom of the array, as indicated by another grey oval, are stimulated by a second IPG. FIG. 11B depicts an oscilloscope trace from the bottom electrode pair, which displays no evidence of waveform interaction from the separate IPG stimulating the top electrode pair. In contrast, FIG. 11C depicts an array of electrodes including two adjacent trios of electrodes, each indicated by grey ovals, and each stimulated by separate IPGs. FIG. 11D depicts an oscilloscope trace from one of the trios of electrodes. The large peaks in the scope trace represent pulses from the traced electrodes, and the small peaks indicate pulses from the adjacent electrodes. FIGS. 11C and 11D indicate that, even when isolated power supplies are used, cross talk can still occur between closely spaced electrodes.

Figure 12A:
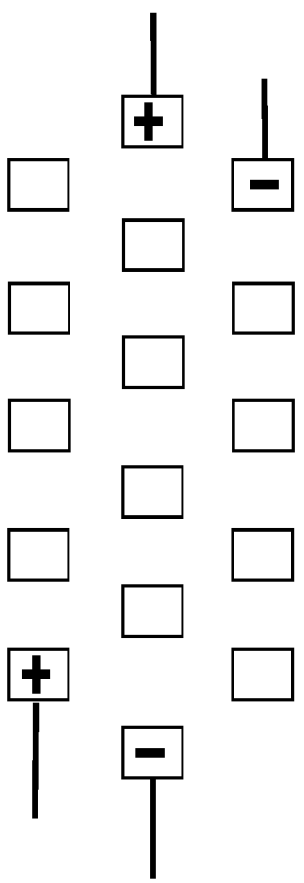
FIG. 12A depicts a schematic of a third electrode array.
Figure 12B:
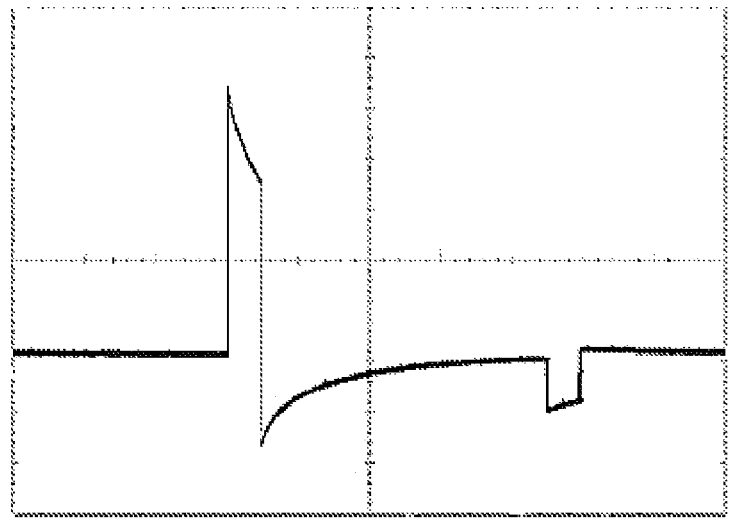
FIG. 12B depicts a first oscilloscope trace from activation of the third electrode array shown in FIG. 12A.
Figure 12C:
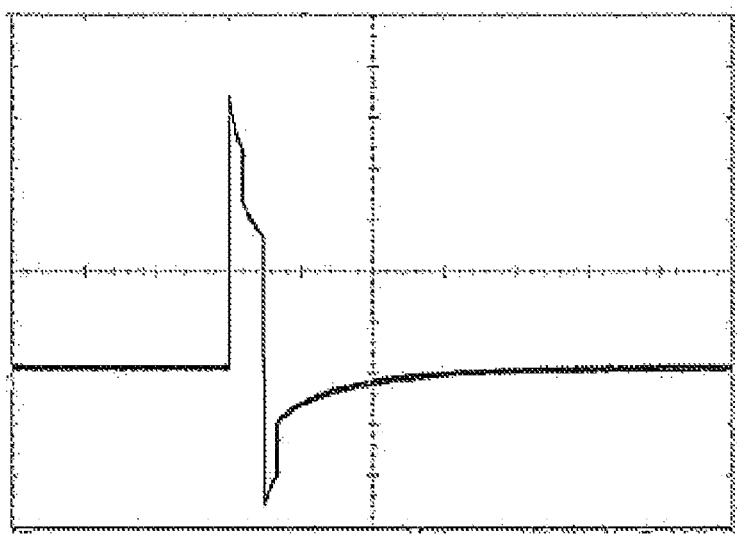
FIG. 12C depicts a second oscilloscope trace from activation of the third electrode array shown in FIG. 12A.

FIG. 12A depicts an array of electrodes wherein a pair of electrodes at the bottom of the array and a pair of electrodes at the top of the array are stimulated using a single IPG having non-isolated power supplies. FIGS. 12B and 12C depict scope traces from the bottom pair of electrodes taken at two different time points. FIG. 12B shows cross talk between the top and bottom electrode pairs, while FIG. 12C shows no cross talk. Taken as a whole, FIGS. 11A-12C indicate that waveform interactions can be avoided by stimulating electrodes using independent and isolated power supplies when those electrodes are not in close physical proximity to each other.

A sixth method of managing waveform interactions includes the use of anodes or cathodes at a fixed potential to provide shielding of the electric field between independent and simultaneous waveforms. Using common ground electrodes physically positioned between stimulation electrodes to shield and separate the stimulation electrodes can effectively compare to managing waveform interactions by using isolated power supplies. It can minimize the interference of two overlapping pulses from two different stimulation electrodes. Test results show that the effectiveness of such shield can compare to the results of using electrodes with two isolated power supplies.

Figure 13:
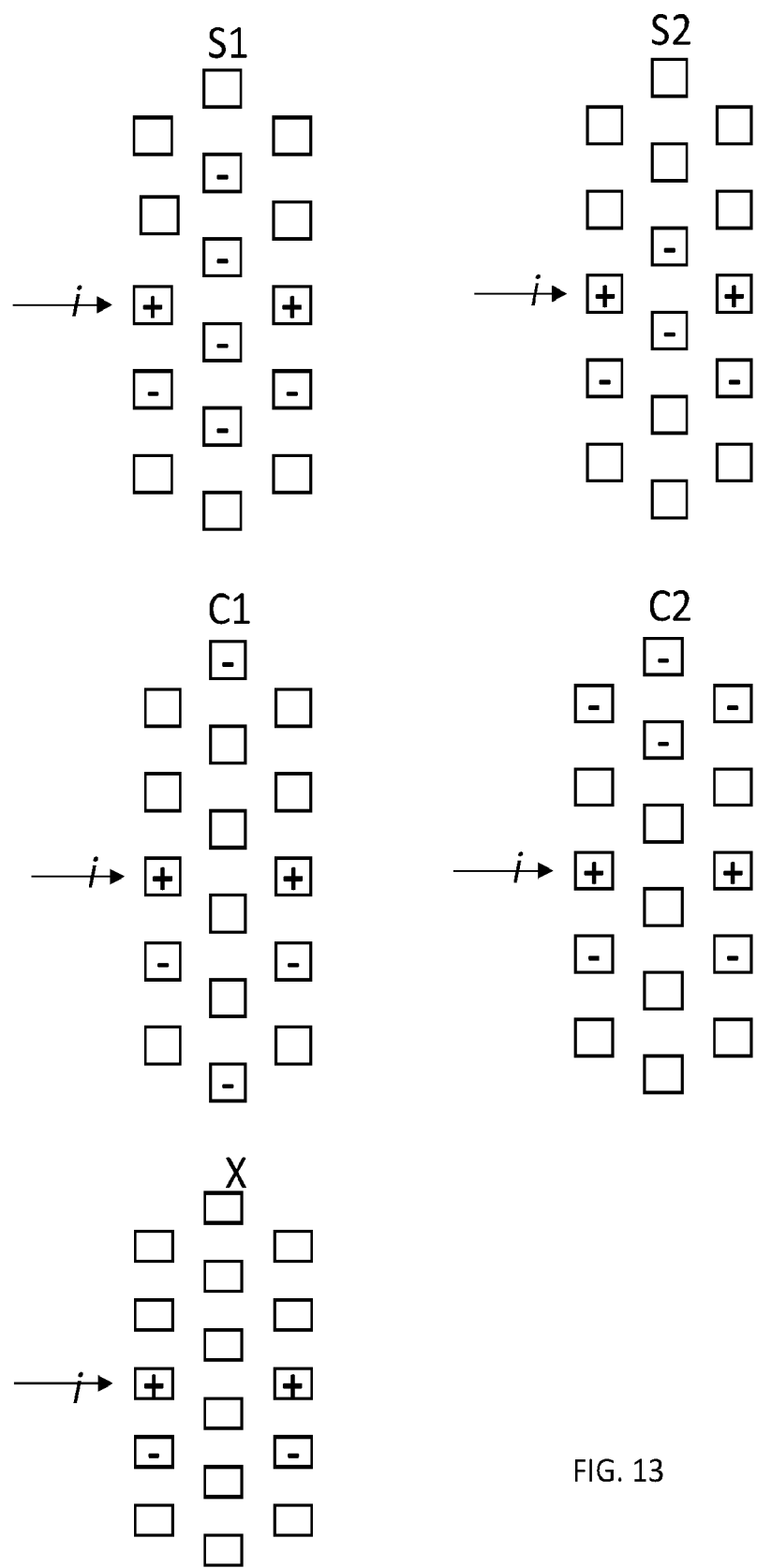
FIG. 13 depicts a series of electrode arrays designated X, S1, S2 and I.
Figure 14:
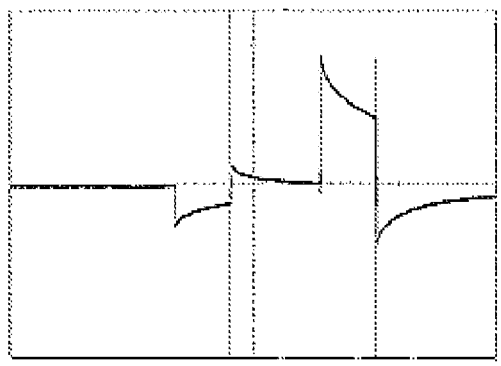
FIG. 14 includes four panels depicting oscilloscope traces from activation of electrode arrays X, S1, S2 and I shown in FIG. 13.
Figure 14:
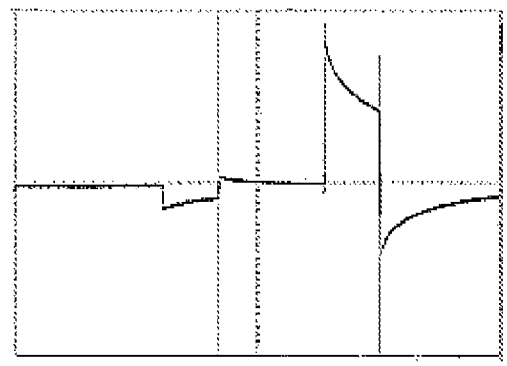
Figure 14:
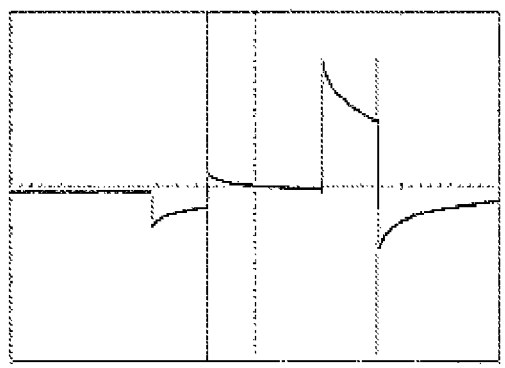
Figure 14:
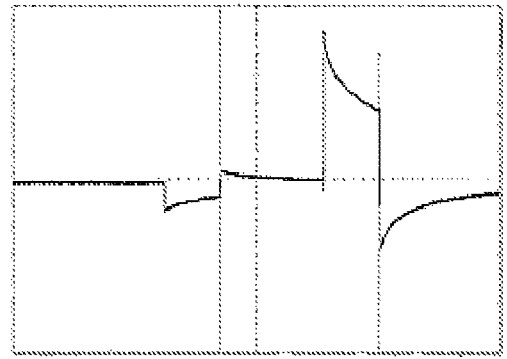

Referring now to FIGS. 13 and 14, FIG. 13 depicts five schematic electrode arrays labeled X, S1, S2, C1 and C2. In each array, current i flows to stimulation cathode electrodes on the left side of the array, and all anodes have equal potential with the ground. Current is measured in electrodes on the right side of the array, whereby measured current indicates current leakage between electrodes. Additional anodes serving as ground electrodes are positioned between the stimulation and measurement electrodes in arrays S1 and S2 serving as shielding electrodes. Additional anodes serving as ground electrodes are also present in arrays C1 and C2, but such additional anodes are not positioned between the stimulation and measurement electrodes. No additional anodes are present in array X. Each array uses a single, non-isolated power supply. FIG. 14 depicts waveforms from oscilloscope measurements of arrays S1, S2, C1 and C2. All tests were performed with the Medtronic Specify™ 5-6-5 electrode array in 1.6 mM buffer solution. In array X, with no shielding electrodes, 3.925 mA of current are generated across the 2 electrodes on the left and 1.15 mA are measurable on the 2 electrodes on the right, which evidences current leakage or interaction of 29% from one side of the electrode array to the other. In array S1, 4.636 mA of current are generated across the 2 electrodes on the left and 0.488 mA are measurable on the 2 electrodes on the right, which evidences a current leakage of 10% in the array including 4 shielding electrodes. In array S2, 4.312 mA of current are generated across the 2 electrodes on the left and 0.575 mA are measurable on the 2 electrodes on the right, which evidences a current leakage of 13% in the array including two shielding electrodes. In array C1, 4.246 mA of current are generated across the 2 electrodes on the left and 0.775 mA are measurable on the 2 electrodes on the right, which evidences a current leakage of 18% in the array including 2 non-shielding electrodes. In array C2, 4.126 mA of current are generated across the 2 electrodes on the left and 0.793 mA are measurable on the 2 electrodes on the right, which evidences a current leakage of 19% in the array including four non-shielding electrodes. Overall, this experiment confirms that inclusion of non-shielding electrodes can decrease current leakage and inclusion of shielding electrodes can significant decrease current leakage between nearby, but not adjacent, stimulation electrodes. For comparison, use of separate and isolated power supplies with adjacent electrodes, as in FIGS. 11C and 11D, resulted in a current leakage of 12% and an identical electrode arrangement using a single power supply resulted in a current leakage of 33%.

Various aspects of different embodiments of the present invention are expressed in paragraphs X1, X2, and X3 as follows:

X1. One aspect of the present invention pertains to a method for providing optimized neurostimulation, including providing an electrode array configured to generate at least two simultaneous waveforms, each waveform including a frequency, a charge balance time, a phase and at least one pulse; optimizing at least one of the at least two simultaneous waveforms to reduce pulse collisions by at least one of altering the phase of the waveform, altering the frequency of the waveform, optimizing the charge balance time of the waveform, delaying a pulse of the waveform, and blanking a pulse of the waveform; and activating the electrode array to generate the at least two simultaneous waveforms.

X2. Another aspect of the present invention pertains to a method for providing optimized neurostimulation, including providing an electrode array comprising a plurality of electrodes, wherein the plurality of electrodes are divided into at least two groups of electrodes, and wherein the electrode array is configured to generate at least two simultaneous waveforms; providing a power source for each group of electrodes, each power source being electrically isolated and physically separate from each other power source; and activating the electrode array to generate the at least two simultaneous waveforms.

X3. A further aspect of the present invention pertains to a method for providing optimized neurostimulation, including providing an electrode array comprising a plurality of electrodes; grouping the plurality of electrodes into a first group including at least one electrode configured to generate a first waveform, a second group including at least one electrode configured to generate a second waveform, and a third group including at least one electrode with a fixed potential, wherein the third group is located between the first group and the second group; and activating the electrode array to generate at least one of the first waveform and the second waveform.

Yet other embodiments pertain to any of the previous statements X1, X2, or X3 which are combined with one or more of the following other aspects.

The method further comprising identifying one of the at least two simultaneous waveforms as a high priority waveform, and wherein the optimizing is applied to a waveform other than the high priority waveform.

Wherein said optimizing includes at least two of altering the phase of the waveform, altering the frequency of the waveform, optimizing the charge balance time of the waveform, delaying a pulse of the waveform, and blanking a pulse of the waveform.

Wherein optimizing the charge balance time of the waveform includes at least one of increasing a recharge period, decreasing a recharge period, increasing a shorting period, and decreasing a shorting period.

Wherein optimizing the charge balance time of the waveform includes at least one of decreasing a recharge period and decreasing a shorting period.

The method further comprising transmitting the at least two simultaneous waveforms to a receiver in communication with a processor, the processor being in communication with the electrode array.

Wherein the electrode array is implanted in a patient.

Wherein the transmitting occurs before the activating and after the optimizing.

Wherein the transmitting occurs before the activating.

Wherein the optimizing occurs before the activating.

Wherein the optimizing occurs before the activating and after the transmitting.

Wherein each of the at least two simultaneous waveforms includes non-identical frequencies.

Wherein altering the phase of the waveform includes delaying the phase of the waveform.

Wherein altering the frequency of the waveform includes increasing or decreasing the frequency of the waveform.

Wherein, for each group of electrodes, each electrode within the group shares a common frequency and pulse width.

Wherein the electrode array is implanted in a patent.

Wherein the first group, the second group, and the third group each include at least two electrodes.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A method for providing optimized neurostimulation, comprising:
   determining, using a computing device, a number of pulse collisions between at least two simultaneous waveforms, each waveform including a frequency, a charge balance time, a phase and at least one pulse,
      wherein the at least one pulse includes, in sequence, a wait period, a charge pulse, an inter-pulse delay, a recharge pulse, and a shorting period, and
      wherein the charge balance time is a combined duration of the recharge pulse and the shorting period;
   optimizing, using the computing device, at least one of the at least two simultaneous waveforms to reduce pulse collisions between the at least two simultaneous waveforms by at least one of
      altering the phase of the waveform,
      changing the frequency of the waveform between two non-identical frequencies, and
      optimizing the charge balance time of the waveform, and
   activating an electrode array, using a pulse generator, to generate the at least two simultaneous waveforms.

2. The method of claim 1, further comprising identifying, using the computing device, one of the at least two simultaneous waveforms as a higher priority waveform, and wherein the optimizing is applied to a waveform other than the higher priority waveform.

3. The method of claim 2, wherein the computing device is a neurostimulator controller in communication with the pulse generator, and wherein the identifying is performed by the controller based on predetermined criteria, and wherein the optimizing is performed by the controller.

4. The method of claim 3, further comprising, prior to the determining, the neurostimulator controller receiving the at least two simultaneous waveforms.

5. The method of claim 2, wherein the computing device is a technical user interface, and wherein the identifying is performed by a user of the technical user interface, and wherein the optimizing is performed using the technical user interface.

6. The method of claim 2, wherein the optimizing is not applied to the higher priority waveform.

7. The method of claim 1, wherein said optimizing includes at least two of
   altering the phase of the waveform,
   changing the frequency of the waveform between two non-identical frequencies,
   optimizing the charge balance time of the waveform,
   delaying a pulse of the waveform, and
   blanking a pulse of the waveform;
wherein one of the at least two is altering the phase of the waveform, changing the frequency of the waveform between two non-identical frequencies, or optimizing the charge balance time of the waveform.

8. The method of claim 1, wherein optimizing the charge balance time of the waveform includes at least one of
   increasing a recharge pulse duration,
   decreasing a recharge pulse duration,
   increasing a shorting period, and
   decreasing a shorting period.

9. The method of claim 8, wherein optimizing the charge balance time of the waveform includes at least one of
   decreasing a recharge pulse duration and
   decreasing a shorting period.

10. The method of claim 8, wherein optimizing the charge balance time of the waveform includes at least one of increasing a recharge pulse and decreasing a recharge pulse.

11. The method of claim 1, further comprising transmitting the at least two simultaneous waveforms from the computing device to a receiver in communication with a processor, the processor being in communication with the pulse generator and the electrode array.

12. The method of claim 11, wherein the electrode array is implanted in a patient.

13. The method of claim 11, wherein the transmitting occurs before the activating and after the optimizing.

14. The method of claim 1, wherein each of the at least two simultaneous waveforms includes non-identical frequencies.

15. The method of claim 1, wherein each waveform further includes a period, and wherein altering the phase of the waveform includes:
   delaying the phase of the waveform by an increment;
   recalculating the number of pulse collisions;
   repeating the previous two steps until the increment reaches the period of the one of the at least two simultaneous waveforms with a highest frequency;

correcting the waveform to include the phase delay resulting in a lowest number of calculated pulse collisions.

16. The method of claim 1,
wherein the electrode array includes a plurality of electrodes disposed on a biocompatible material, wherein the plurality of electrodes on the biocompatible material are divided into at least two groups of electrodes, and wherein the electrode array is configured to generate at least two simultaneous waveforms; and wherein the pulse generator includes one pulse generator for each group of electrodes, each pulse generator being electrically isolated and physically separate from each other pulse generator.

17. The method of claim 16, wherein, for each group of electrodes, each electrode within the group is activated with a common frequency and pulse width.

18. The method of claim 1, wherein changing the frequency of the waveform between two non-identical frequencies includes, when a pulse collision is determined, changing the frequency of the waveform from a pre-determined first frequency to a pre-determined second frequency, maintaining the waveform at the second frequency until a subsequent pulse collision is determined, then reverting the frequency of the waveform to the first frequency, the first frequency and second frequency being non-identical frequencies, to reduce pulse collisions.

19. The method of claim 1, wherein changing the frequency of the waveform between two non-identical frequencies includes, when a pulse collision is determined, alternating the frequency of the waveform from a first frequency to a second frequency, maintaining the waveform at the second frequency until a subsequent pulse collision is determined, then alternating the frequency of the waveform from the second frequency to the first frequency, the first frequency and second frequency being non-identical frequencies, to reduce pulse collisions.

\* \* \* \* \*